United States Patent
Newsome et al.

(10) Patent No.: US 6,863,782 B2
(45) Date of Patent: Mar. 8, 2005

(54) METHOD OF PREPARING DI(KETENE ACETALS)

(75) Inventors: Peter W. Newsome, Horse Shoe, NC (US); A. Roger Frisbee, Hendersonville, NC (US); Zinovy Itov, Arden, NC (US); April J. Morgan, Fletcher, NC (US); Robert A. Noe, Mountain Home, NC (US)

(73) Assignee: A.P. Pharma, Inc., Redwood City, CA (US)

( * ) Notice: Subject to any disclaimer, the term of this patent is extended or adjusted under 35 U.S.C. 154(b) by 264 days.

(21) Appl. No.: 10/298,188

(22) Filed: Nov. 15, 2002

(65) Prior Publication Data

US 2004/0097742 A1 May 20, 2004

(51) Int. Cl.[7] .............................................. C07C 45/00
(52) U.S. Cl. .............................. 204/157.93; 204/157.69
(58) Field of Search ........................ 204/157.93, 157.69

(56) References Cited

U.S. PATENT DOCUMENTS

| 4,304,767 A | 12/1981 | Heller et al. | 424/78 |
| 4,513,143 A | 4/1985 | Ng et al. | 549/335 |
| 4,532,335 A | 7/1985 | Helwing | 549/335 |

FOREIGN PATENT DOCUMENTS

| DE | 2331675 | 5/1974 | |
| DE | 2331675 B | * 5/1974 | ........... C07C/43/30 |

OTHER PUBLICATIONS

Corey et al., "Selective cleavage of allyl ethers under mild conditions by transition metal reagents", *J. Org. Chem.*, 38(18), 3224 (1973), no month.

Carvello et al., "Kerene acctal monomers: synthesis and characterization", *J. Polymer Sci.. Part A: Polymer Chemistry*, 34, 3091–3102 (1996), no month.

Haworth, "XXXII. Cs– and *trans*–tetramethylene–(1:3)–dicarboxylic acids and the condensation of formaldehyde with ethylic malonate", *J. Chem. Soc.*, 73, 330–345 (1898), no month.

Haydock et al., "3,3'–Edylenediglutarimide as a potential rumor inhibitor", *J. Med. Chem.*, 15, 44.448 (1972), no month.

Meineke et al., "The ccylization of certain ethylene dimalonie esters by sodium ethoxide", *J. Amer. Chem. Soc.*, 57. 1133 (1935), no month.

* cited by examiner

*Primary Examiner*—Edna Wong
(74) *Attorney, Agent, or Firm*—Heller Ehrman White & McAuliffe LLP

(57) ABSTRACT

Di(ketene acetals) are prepared by photoisomerizing the corresponding di(vinyl acetals).

15 Claims, No Drawings

METHOD OF PREPARING DI(KETENE ACETALS)

BACKGROUND OF THE INVENTION

1. Field of the Invention

This invention relates to a method of preparing di(ketene acetals).

2. Description of the Related Art

Corey et al., *J. Org. Chem.*, 38, 3224 (1973), discloses the isomerization of the allyl ethers of menthol, decanol, and cholesterol to the corresponding 1-propenyl ethers under neutral aprotic conditions catalyzed with tris(triphenylphosphine)rhodium chloride, and the ready hydrolysis of these 1-propenyl ethers to the original alcohols at pH 2.

U.S. Pat. No. 4,304,767 discloses the preparation of a number of di(ketene acetals), such as 3,9-dimethylene-2,4,8,10-tetraoxaspiro[5.5]undecane (the di(ketene acetal) of pentaerythritol), 2,6-dimethylenehexahydrobenzo[1,2-d,4,5-d']bis[1,3]dioxole (the di(ketene acetal) of 1,2,4,5-cyclohexanetetraol), 1,2-ethylenebis(2-methylene-[1,3]dioxolane] (the di(ketene acetal) of 1,2,5,6-hexanetetraol), and alkylated di(ketene acetals) such as 2,6-diisopropylidenehexahydrobenzo[1,2-d,4,5-d']bis[1,3]dioxole, 3,9-di-sec-butylidene-2,4,8,10-tetraoxaspiro[5.5]undecane, and 3,9-diisopropylidene-2,4,8,10-tetraoxaspiro[5.5]undecane, by methods which include the isomerization of the di(vinyl acetals); and the preparation of poly(ortho esters) from these and related di- and tri-(ketene acetals) by reaction of the compounds with diols or polyols.

U.S. Pat. No. 4,513,143 discloses the preparation of ketene acetals and di(ketene acetals), such as 3,9-diethylidene-2,4,8,10-tetraoxaspiro[5.5]undecane (DETOSU), by the isomerization of the corresponding di(vinyl acetals) in alkali metal lower n-alkyl/water soluble primary amine solutions.

U.S. Pat. No. 4,532,335 discloses the preparation of ketene acetals and di(ketene acetals), such as DETOSU and 3,9-diisopropylidene-2,4,8,10-tetraoxaspiro[5.5]undecane, by the isomerization of the corresponding di(vinyl acetals) in alkali metal alkoxide/ethyleneamine solutions.

Crivello et al., *J. Polymer Sci., Part A: Polymer Chemistry*, 34, 3091–3102 (1996), discloses the preparation of a number of ketene acetals and di(ketene acetals), including 2,2'-diethylidene-4,4'-bis-[1,3]dioxolane) and DETOSU, in each case by the preparation of the corresponding di(vinyl acetal) from the relevant tetraol and acrolein and isomerization with tris(triphenylphosphine)-ruthenium dichloride.

German Patent No. 2 331 675 (*Chem. Abs.*, 81:63153v (1974)) discloses the preparation of aliphatic ketene acetals by the isomerization of unsaturated aldehyde acetals having a double bond in the α-, β-, or γ-position of the acetal group with iron carbonyls and/or actinic light. In six examples, 2-vinyl-[1,3]-dioxolane was photoisomerized to methylketene ethylene ketal in the presence of iron pentacarbonyl and N,N-dimethylaniline; diiron nonacarbonyl, N,N-dimethylaniline and hydroquinone monomethyl ether; iron pentacarbonyl and n-octane; and triiron dodecacarbonyl; while acrolein dimethyl acetal was photoisomerized to methylketene dimethyl acetal in the presence of iron pentacarbonyl, and diiron nonacarbonyl.

SUMMARY OF THE INVENTION

This invention is a method for preparing di(ketene acetals) by photoisomerizing the corresponding di(vinyl acetals).

DETAILED DESCRIPTION OF THE INVENTION

Starting Materials

The di(vinyl acetals) that are the starting materials for the method of this invention may be commercially available or may be prepared by methods known to a person of ordinary skill in the art.

Di(vinyl acetals) that are of particular interest are those used to form di(ketene acetals) usable in the preparation of poly(ortho esters) and copolymers containing those poly (ortho esters). Such di(vinyl acetals) include compounds of the formulae:

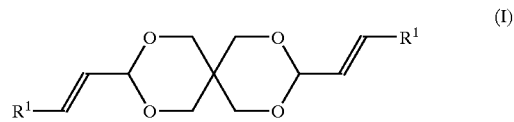  (I)

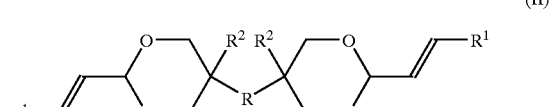  (II)

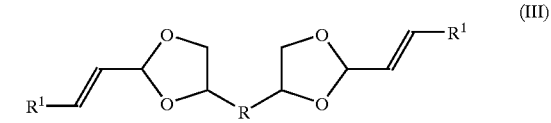  (III)

where:
R is a bond, —(CH$_2$)$_a$—, or —(CH$_2$)$_b$—O—(CH$_2$)$_c$—; where a is an integer of 1 to 10, and b and c are independently integers of 1 to 5;
R$^1$ is hydrogen or a C$_1$–C$_2$ alkyl, and
R$^2$ is hydrogen or a C$_1$–C$_2$ alkyl.

A typical method for the synthesis of these di(vinyl acetals) is the condensation of a bis(diol) of the formulae IV, V, or VI:

  (IV)

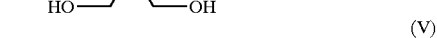  (V)

  (VI)

with two equivalents of a vinylic aldehyde, such as acrolein or crotonaldehyde, or their dialkyl acetals, such as acrolein dimethyl acetal or diethyl acetal, and such condensation reactions are well known and are discussed in the references listed in the "Description of the related art" section of this application. For example, Crivello et al. discloses the synthesis of the compound of formula I where each R$^1$ is hydrogen and the synthesis of the compound of formula III where R is a bond and each R$^1$ is hydrogen.

The bis(diol) of formula IV is pentaerythritol. Its reaction product with acrolein, 3,9-divinyl-2,4,8,10-tetraoxaspiro[5.5]undecane, is available from suppliers such as Aldrich Chemical Co. and TCI America.

The bis(diol) of formula V where R is a bond and each R$^2$ is hydrogen may be prepared by the reduction of the tetramethyl 1,1,2,2-ethanetetracarboxylate, available from Aldrich, with a reducing agent such as LiAlH$_4$ in a solvent such as diethyl ether, preferably at reduced temperature such as 0° C., to give the bis(diol). A reduction of this type is described in Haydock et al., *J. Med. Chem.*, 15:447–448 (1972) for the reduction of tetraethyl 1,1,4,4-butanetetracarboxylate.

The bis(diol) of formula V where R is —(CH$_2$)$_a$— and each R$^2$ is hydrogen may be prepared by the reaction of an α,ω-dihaloalkane of the formula X—(CH$_2$)$_a$—X, where X is Cl or Br, such as 1,3-dibromopropane or 1,5-dibromopentane, with a dialkyl malonate of the formula CH$_2$(COOR$^3$)$_2$ where R$^3$ is C$_1$–C$_4$ alkyl, in the presence of a strong base such as an alkali metal or alkaline earth alkoxides (e.g. sodium or magnesium ethoxide) in a solvent such as a lower alkanoyl (e.g. ethanol) to give the tetraalkyl α,α,ω,ω-alkanetetracarboxylate. A coupling of this type is described in Meincke et al., *J. Amer. Chem. Soc.*, 57, 1133 (1935) for the preparation of tetraethyl 1,1,4,4-butanetetracarboxylate from diethyl malonate and 1,2-dibromoethane in the presence of magnesium ethoxide in ethanol. The thus-formed tetracarboxylate is then reduced to give the bis(diol). Other bis(diols) where each R$^2$ is non-hydrogen may be prepared from the corresponding dialkyl alkylmalonates, also available from Aldrich. The bis(diol) of formula IV where R is —CH$_2$— and each R$^2$ is hydrogen may also be prepared by the reaction of formaldehyde and a dialkyl malonate, such as diethyl malonate, as described by Haworth, *J. Chem. Soc.*, 73:330–345 (1898), followed by reduction of the thus-formed tetraethyl 1,1,3,3-propanetetracarboxylate to give the bis(diol).

The bis(diols) of formula V where R is —(CH$_2$)$_b$—O—(CH$_2$)$_c$— may be prepared by a similar process, replacing the α,ω-dihaloalkane with a di(ω-haloalkyl) ether of the formula X—(CH$_2$)$_b$—O—(CH$_2$)$_c$—X, where X is Cl or Br.

The bis(diol) of formula V where R is —CH$_2$—O—CH$_2$— and each R is ethyl is di(trimethylolpropane) and is available from Aldrich and from Perstorp. Di(vinyl acetals) of formula II where R is —CH$_2$—O—CH$_2$— and each R$^2$ is hydrogen, methyl, or ethyl may also be prepared from the commercially available trimethylolmethane, trimethylolethane, and trimethylolpropane in the following manner:

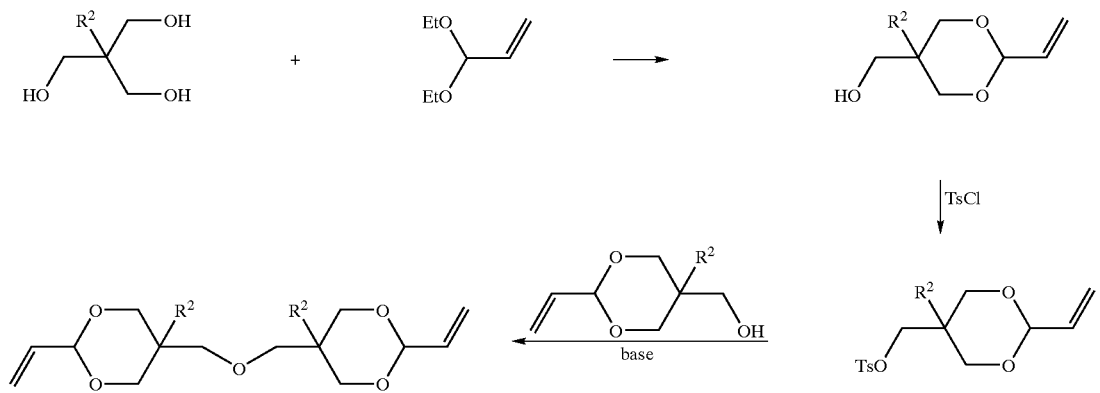

where the trimethylolalkane is first converted to the vinyl acetal by reaction with a vinylic aldehyde or its dialkyl acetal (acrolein diethyl acetal is shown), then some of the resulting alcohol converted to a leaving group such as the tosylate (shown) or other alkane- or arenesulfonate, and that compound treated with base and the alcohol to form the di(vinyl acetal).

The bis(diol) of formula VI where R is a bond is erythritol. The bis(diol) of formula VI where R is —(CH$_2$)$_a$— may be prepared by the oxidation of an α,ω-diene, such as 1,3-butadiene or 1,5-hexadiene, with an oxidizing reagent such as osmium tetroxide/hydrogen peroxide, or by other methods known in the art, to give the bis(diol). The bis(diol) of formula VI where R is —(CH$_2$)$_b$—O—(CH$_2$)$_c$— may be prepared by the reaction of an ω-hydroxy-α-olefin, such as allyl alcohol, with an ω-haloalkyloxirane, such as epichlorohydrin, to form an ω-epoxy-α-olefin with the backbone interrupted by an oxygen atom, such as 2-allyloxymethyloxirane, which is then oxidized with an oxidizing reagent such as osmium tetroxide/hydrogen peroxide, or by other methods known in the art, to give the bis(diol).

Variations on these methods, and other suitable methods for the preparation of the bis(diols) and the di(vinyl acetals), will be available to a person of ordinary skill in the art having regard to that skill and this disclosure.

Solvents

The photoisomerization is desirably carried out in an inert solvent, by which is meant a solvent that is inert to the starting di(vinyl acetal), the sensitizer, the product di(ketene acetal), and other intermediates and products that are formed during the photoisomerization under the reaction conditions, that is photochemically inert, and that does not significantly absorb UV light at above about 300 nm. A desirable solvent is one that, in addition to being inert, is an effective solvent for the reaction mixture, is readily degassed (because the preferred iron pentacarbonyl sensitizer is destroyed by oxygen), and is easily removed from the product ketene acetal. Suitable such solvents are hydrocarbons, especially aliphatic hydrocarbons such as the alkanes (straight, branched, and cyclic); and preferred solvents are the C$_5$–C$_8$ alkanes, such as the various pentanes, hexanes, heptanes, and octanes, and mixtures thereof. Other suitable solvents include ethers such as diethyl ether, tetrahydrofuran, and dioxane.

Sensitizers

Sensitizers for the photoisomerization are those capable of energizing the isomerization of the di(vinyl acetal) to the corresponding di(ketene acetal) with minimal catalysis of side reactions such as the formation of undesired isomeric products or polymers. Suitable such sensitizers are transition metal organometallic compounds, such as iron organometallic compounds. Transition metal carbonyls (such as the iron carbonyls, e.g. iron pentacarbonyl, diiron nonacarbonyl, and triiron dodecacarbonyl) and mixed carbonyls (e.g. mixed π-cyclopentadienyl carbonyls, such as cyclopentadienylmanganese tricarbonyl) are desirable sensitizers, and a preferred sensitizer is iron pentacarbonyl, for its low cost, efficiency in catalysis, and its easy destruction by oxidation with air after completion of the photoisomerization. The sensitizer may be employed in any quantity necessary or desirable for the speed and selectivity of the photoisomerization: a suitable range is 0.001–10.0 mol %, particularly 0.01–1.0 mol %, and more particularly about 0.1–0.5 mol %, based on the di(vinyl acetal).

The Photoisomerization

The details of the photoisomerization step and apparatus used will depend somewhat on the scale of the reaction contemplated, but in general the reaction will proceed at between room temperature and the boiling point of the solvent used in the photoisomerization, under an inert atmosphere, such as under nitrogen or argon. The reaction mixture will typically be stirred or otherwise agitated during the reaction. A suitable light source for the photoisomerization step is a medium pressure mercury lamp of the type commonly used for photochemical reactions, or a high pressure mercury or xenon lamp, emitting light of 200–700 nm, especially 200–550 nm wavelength. Suitable commercial apparatus for the performance of photochemical reactions is readily commercially available from suppliers such as Ace Glass Incorporated, Vineland N.J., USA, or through such reagent suppliers as Aldrich Chemical Company.

Typically, the di(vinyl acetal) and a sensitizer will be dissolved in a suitable solvent, such as an alkane, and the mixture refluxed under nitrogen, during which time it is irradiated with a medium pressure mercury lamp for from a few minutes to a few hours, e.g. from 30 minutes to two hours. The progress of the reaction may be monitored by such analytical techniques as gas chromatography, HPLC, NMR, and IR, looking for the disappearance of signals indicative of the starting di(vinyl acetal) or its vinyl group(s) and the appearance of signals indicative of the product di(ketene acetal) or its ketene group(s), and the irradiation time prolonged or shortened accordingly.

The reaction mixture also optionally contains a tertiary amine where the amine nitrogen is substituted with $C_1$–$C_6$ alkyl, $C_5$–$C_8$ cycloalkyl, or phenyl, such as tributylamine, trimethylamine, N,N-dimethylcyclohexylamine, N,N-dimethylaniline, and the like; or a heterocyclic amine such as N-methylpyrrolidine, diazabicyclo[2.2.2]octane, and the like, at a concentration of up to 5 wt. %, e.g. 0.5–5 wt. %, with respect to the starting di(vinyl acetal). It also optionally contains a polymerization inhibitor at a concentration of up to 1 wt. %, e.g. 0.01–1 wt. %, with respect to the starting di(vinyl acetal). Suitable polymerization inhibitors, if present, are those compounds commonly used for the stabilization of reactive monomers, such as hydroquinone and its monomethyl ether.

On completion of the photoisomerization, the sensitizer is typically removed or, in the case of the iron carbonyls, destroyed by dry air oxidation.

Purification of the di(ketene acetals)

Purification of the di(ketene acetals) that are the product of the photoisomerization method of this invention may be accomplished by any suitable method among those purification methods for organic compounds known to the person of ordinary skill in the art. Typical purification methods include concentration of the product in the reaction mixture by distillation of the solvent (for example, under atmospheric or reduced pressure) and purification by chromatography, short path distillation, and crystallization, as appropriate to the di(ketene acetal) being prepared. The purity of the di(ketene acetals) may be determined by conventional methods of analysis such as gas chromatography, HPLC, NMR, and by comparison of melting or boiling points or spectral data with authentic samples of the di(ketene acetals) prepared by other methods.

EXAMPLES

Example 1

Preparation of 3,9-diethylidene-2,4,8,10-tetraoxaspiro[5.5]undecane, DETOSU, 1

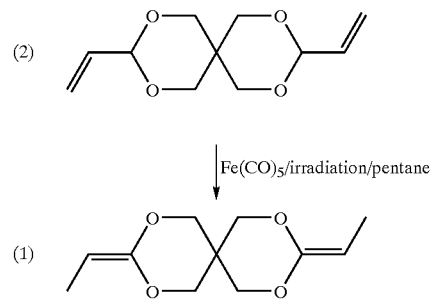

To a clean, dry 22 L photochemical reactor fitted with a thermowell, condenser, and mechanical stirrer, under nitrogen atmosphere was added 10 L pentane and 2072 g (9.76 mol) 3,9-divinyl-2,4,8,10-tetraoxaspiro[5.5]undecane, 2. The mixture was stirred at reflux for 40 minutes to degas the solvent, then 5.9 mL (8.79 g, 44.9 mmol, 0.45 mol %) iron pentacarbonyl was added, and the solution refluxed for an additional 15 minutes. The resulting solution was refluxed under irradiation with a 450 W medium pressure quartz mercury vapor UV lamp (Ace-Hanovia) in a reflector housing for 30 minutes, refluxed without irradiation for 90 minutes, refluxed under irradiation for 40 minutes, and refluxed without irradiation for 6 hours, by when GC showed that the starting material had been consumed and the amount of partially isomerized material was less than 5%. The reaction mixture was allowed to cool overnight while stirring, still under nitrogen atmosphere. About 10% (1 L) of the cooled reaction mixture was removed and used for in-process analysis. To the reactor containing the remaining 90% of the reaction mixture was added 50 mL triethylamine, and most of the pentane was removed by distillation under nitrogen atmosphere at atmospheric pressure with a pot temperature of 30–40° C. The crude DETOSU, 1, wet with solvent, about 3.5 L, was dried (pressure 1–3 mbar, pot temperature 45–50° C.) to give 1.9 Kg dried crude DETOSU (100% crude yield, 5% partially isomerized material by GC); and this was distilled in a short-path distillation apparatus with boiling chips (pressure ~3 mbar, pot temperature 124–165° C., head temperature 121–129° C.) to give 1762 g distilled crude DETOSU.

To a clean, dry 22 L flask fitted with a thermowell, condenser, and mechanical stirrer, under a nitrogen atmosphere was added the distilled crude DETOSU from the previous paragraph, 10.6 L heptane, and 10 mL triethylamine. The mixture was heated to dissolution (~80° C.) with stirring, and allowed to cool to room temperature overnight, still under nitrogen atmosphere. Some gummy brown material was noticed adhering to the walls of the flask and thermowell; so the solution was decanted and the apparatus cleaned before returning the solution to the flask. The solution was reheated to 80° C., resulting in a slightly cloudy solution, then cooled to −10° C. and crystallization started by scratching the inside of the flask walls with a glass rod. The solution warmed about 4° C. during crystallization before returning to −10° C. over about one hour. The mixture was held at −10° C. for an additional hour, then cooled to −20° C. and held for 15 minutes. The crystalline DETOSU was collected by cold centrifugation, using a WESTERN STATES® Model 1000-1476 perforated basket laboratory centrifuge fitted with a 60 μm filter bag, under nitrogen atmosphere. The centrifuge was precooled with 4 L of −30° C. pentane while rotating, then the crystalline DETOSU slurry added under 100–160×g, ensuring that excessive liquid did not accumulate in the basket. The centrifuge speed was increased to ~1000×g to dry the filter cake, which was then washed with 2.5 L of −30° C. pentane and centrifugation continued for an additional 30 minutes. A first crop of 927 g (54% yield, 2.8% partially isomerized material by GC) crystalline DETOSU was obtained. A second crop of 527 g was obtained from the mother liquor by a similar process, giving a total of 1513 g (82% yield) of crystalline DETOSU. The crystalline DETOSU was recrystallized using 8.5 L pentane and 8.5 mL triethylamine to give 982 g recrystallized DETOSU in the first crop; and this was distilled (pressure ~3 mbar, pot temperature 129–145° C., head temperature 121–129° C.) to give 879 g purified DETOSU, 1 (51% overall yield, $^1$H NMR consistent with structure of clean desired product, 1.7% partially isomerized material by GC).

To 300 mL toluene in an 500 mL flask with condenser under a nitrogen atmosphere were added 30 g (120 mmol) di(trimethylolpropane), 4, 45.6 mL (38.9 g, 300 mmol) acrolein diethyl acetal, and 1.5 g (6 mmol) pyridinium p-toluenesulfonate. The mixture was refluxed for 4 hours, then cooled to room temperature, and 0.67 g (6 mmol) potassium tert-butoxide added. The toluene was removed by evaporation under reduced pressure, and the residue distilled in a Kugelrohr apparatus (pressure 1–3 mbar, pot temperature 142–180° C.) to give 35.35 g (91% yield) of crude di[(5-ethyl-2-vinyl-[1,3]dioxan-5-yl)methyl]ether, 5, as a light yellow oil. The crude product, 30 g, was purified by chromatography on 1 Kg Merck Silica Gel 60 in a 2 L glass fritted funnel, eluting with 20:80 ethyl acetate/heptane, to give 27.8 g (71% yield) of purer product, which was re-purified by a second chromatography on 1 Kg MERCK® Silica Gel 60 in a 2 L glass fritted funnel, eluting with 10:90 ethyl acetate/heptane, to give 16.44 g (42% yield) of essentially pure di[(5-ethyl-2-vinyl-1,3dioxan-5-yl)methyl]ether. This material was used in the photoisomerization.

To 220 mL pentane in a 500 mL photochemical reactor was added 14.32 g (43.9 mmol) di[(5-ethyl-2-vinyl-[1,3]dioxan-5-yl)methyl]ether from the previous step. The solution was refluxed vigorously for 20 minutes to degas it, then 115 µL (171 µg, 0.87 µmol, 0.2 mol %) iron pentacarbonyl was added, and the solution refluxed for an additional 20 minutes. The resulting solution was irradiated for one hour, by when NMR showed no vinyl signals. After cooling to room temperature and the addition of 0.5 mL triethylamine, the solution was sparged with dry air for 4 hours. The pentane was removed by evaporation under reduced pressure, and the residual oil was distilled in a Kugelrohr apparatus (pot temperature 220° C., pressure 1–3 mbar) to give 9.04 g (63% yield) of di[(5-ethyl-2-ethylidene-[1,3]dioxan-5-yl)methyl]ether, 3, as a colorless oil. The identity of the product was confirmed by $^1$H NMR and mass spectra (observed: 363, 345, calculated for $C_{18}H_{35}O_7$ (M+2H$_2$O+H$^+$): 363; calculated for $C_{18}H_{33}O_6$ (M+H$_2$O+H$^+$): 345).

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claim:

1. A method for preparing a di(ketene acetal) comprising photoisomerizing a di(vinyl acetal).

2. The method of claim 1 comprising photoisomerizing the di(vinyl acetal) in the presence of a transition metal organometallic compound.

3. The method of claim 2 where the transition metal organometallic compound is an iron organometallic compound.

4. The method of claim 3 where the iron organometallic compound is iron pentacarbonyl.

5. The method of claim 2 where the concentration of the transition metal organometallic compound is 0.001–10.0 mol % based on the di(vinyl acetal).

6. The method of claim 5 where the concentration of the transition metal organometallic compound is 0.01–1.0 mol % based on the di(vinyl acetal).

7. The method of claim 1 comprising photoisomerizing the di(vinyl acetal) in an inert solvent.

8. The method of claim 7 where the inert solvent comprises an alkane.

9. The method of claim 8 where the inert solvent consists essentially of an alkane.

10. The method of claim 8 where the alkane is a $C_5$–$C_7$ alkane or a mixture of such alkanes.

11. The method of claim 1 where the di(vinyl acetal) is a compound of formula I:

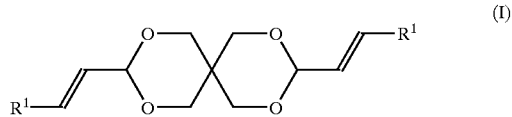

where $R^1$ is hydrogen or a $C_1$–$C_2$ alkyl.

12. The method of claim 11 where the di(vinyl acetal) is 3,9-divinyl-2,4,8,10-tetraoxaspiro[5,5]undecane.

13. The method of claim 1 where the di(vinyl acetal) is a compound of formula II:

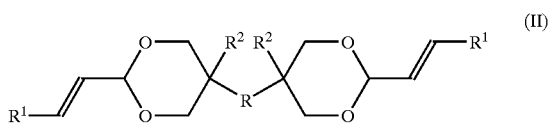

where:

R is a bond, —(CH$_2$)$_a$—, or —(CH$_2$)$_b$—O—(CH$_2$)$_c$—; where a is an integer of 1 to 10, and b and c are independently integers of 1 to 5;

$R^1$ is hydrogen or a $C_1$–$C_2$ alkyl, and $R^2$ is hydrogen or a $C_1$–$C_2$ alkyl.

14. The method of claim 13 where the di(vinyl acetal) is di[(5-ethyl-2-vinyl-[1,3]dioxan-5-yl)methyl]ether.

15. The method of claim 1 where the di(vinyl acetal) is a compound of formula III:

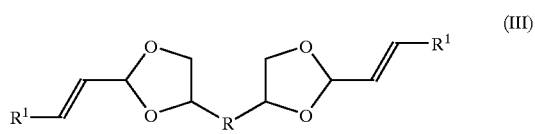

where:

R is a bond, —(CH$_2$)$_a$—, or —(CH$_2$)$_b$—O—(CH$_2$)$_c$—; where a is an integer of 1 to 10, and b and c are independently integers of 1 to 5; and $R^1$ is hydrogen or a $C_1$–$C_2$ alkyl.

* * * * *

UNITED STATES PATENT AND TRADEMARK OFFICE
CERTIFICATE OF CORRECTION

PATENT NO. : 6,863,782 B2
DATED : March 8, 2005
INVENTOR(S) : Newsome et al.

It is certified that error appears in the above-identified patent and that said Letters Patent is hereby corrected as shown below:

Column 7,
Between lines 19 and 20, the Scheme and Example heading should be added as follows:

-- Example 2: Preparation of di[(5-ethyl-2-ethylidene-[1,3]dioxan-5-yl)methyl] ether, 3 --

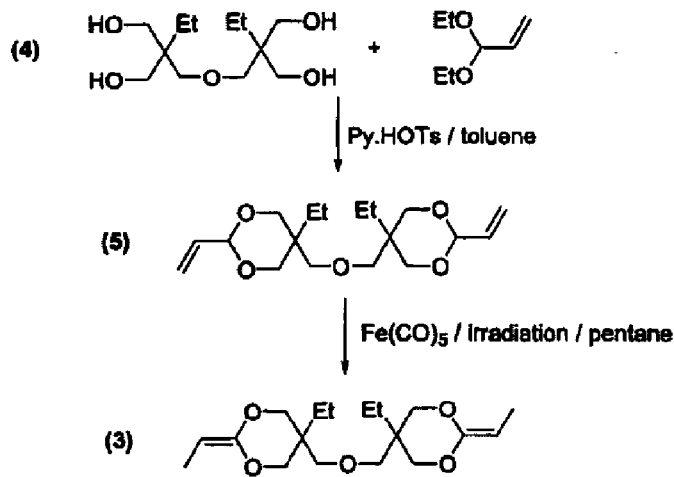

Signed and Sealed this

Seventeenth Day of May, 2005

JON W. DUDAS
*Director of the United States Patent and Trademark Office*